United States Patent [19]

Luiset et al.

[11] Patent Number: 4,690,641
[45] Date of Patent: Sep. 1, 1987

[54] CONTRA-ANGLE OR TURBINE HEAD OF A DENTAL HANDPIECE

[75] Inventors: Jean-Jacques Luiset, Geneva, Switzerland; Michel Seigneurin, Douvaine, France

[73] Assignee: Micro-Mega S.A., Besancon, France

[21] Appl. No.: 825,233

[22] Filed: Feb. 3, 1986

[30] Foreign Application Priority Data

Feb. 4, 1985 [FR] France ................ 85 02145

[51] Int. Cl.$^4$ .............................................. A61C 1/14
[52] U.S. Cl. ...................................... 433/129; 279/75
[58] Field of Search ................. 433/129, 127, 128; 279/75

[56] References Cited

U.S. PATENT DOCUMENTS

| 2,010,210 | 8/1935 | Witt | 433/128 |
| 2,843,388 | 7/1958 | Butler | 279/75 |
| 4,203,222 | 5/1980 | Mattchen | 279/75 |
| 4,436,512 | 3/1984 | Garcia | 433/129 |

Primary Examiner—John J. Wilson
Attorney, Agent, or Firm—Robert E. Burns; Emmanuel J. Lobato

[57] ABSTRACT

A chuck for receiving a plain shank of a dental burr is rotatably mounted in the head of a dental handpiece and is driven by a pinion or by turbine vanes. The chuck comprises a sleeve adapted to receive the shank of a burr and provided with at least one elongate clamping claw which is movable radially between an inner clamping position and an outer releasing position. Facing grooves in the clamping claw and in an actuating member which is movable axially relative to the sleeve define a ramp way for a row of bearing balls. The ramp way extends in a direction which is generally axial but is inclined at an angle of 1° to 4° to the axis so that the clamping claw is moved radially by axial movement of the actuating member. The clamping claw is spring biased to clamping position and is movable to releasing position by a push button for moving the actuating member axially relative to the sleeve and thereby moving the clamping claw radially outwardly.

16 Claims, 18 Drawing Figures

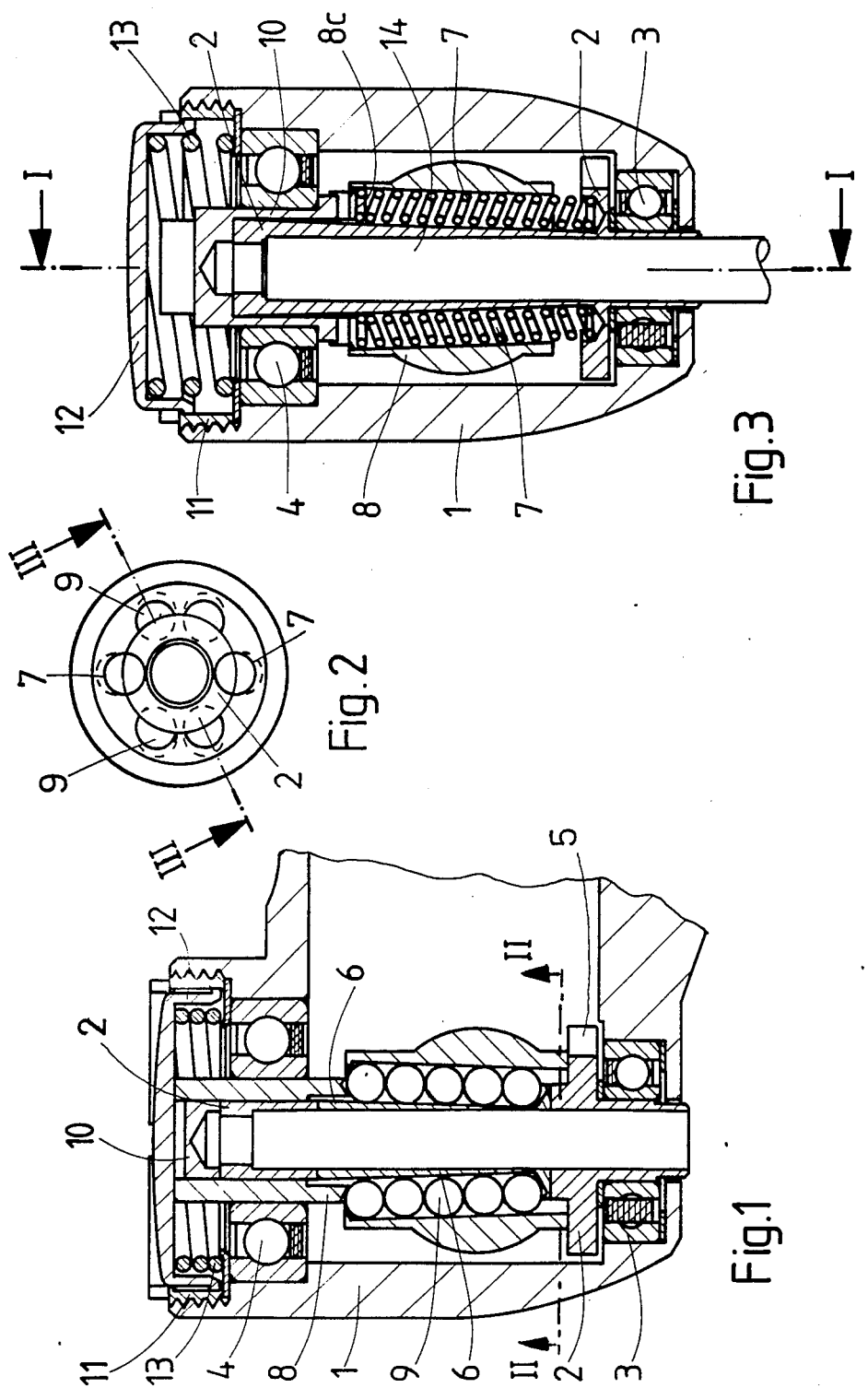

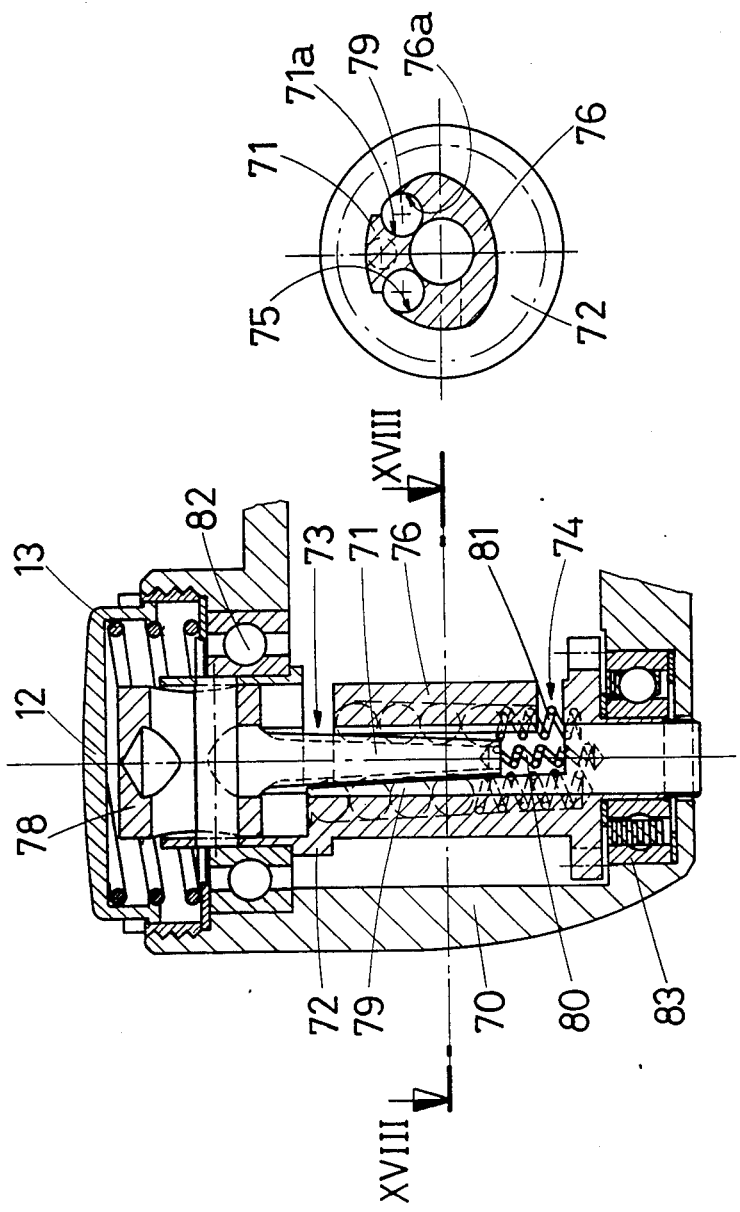

CONTRA-ANGLE OR TURBINE HEAD OF A DENTAL HANDPIECE

BACKGROUND OF THE INVENTION

1. Field of the Invention

The present invention relates to a contra-angle or turbine head of a dental handpiece comprising a sleeve rotatably mounted in the head case and adapted to receive the plain shank of a dental tool, said sleeve being provided with claws movable in the radial direction between a position in which said shank is clamped by resilient means and a position in which said shank is released by an actuator operable against the force of said resilient means.

2. The Prior Art

Many systems have already been proposed with a view to hold the burrs within the contra-angle or turbine heads. In so-called low-speed contra-angle burrs the standardized burrs are provided with a shank having a diameter of 2.35 mm, a circular groove and a flat face to facilitate the holding of the tool in position. On the other hand, so-called high-speed contra-angles and turbines use burrs having a smooth shank 1.6 mm in diameter.

Holding these burrs in position is a difficult problem, for relatively ample tolerances are generally admitted for the shank diameter. Therefore, the clamping means should be capable of exerting a considerable pressure on the shanks so that the latter be firmly held in position, even when their diameter has its smallest tolerance.

According to a relatively old French Pat. No. 1,255,386, it is known to use a clamping jaw consisting of at least two semi-cylindrical, slightly curved shells rigidly coupled to a small bar parallel to the shell generatrices, the shank of the tool being held simply by frictional contact between said shells.

SUMMARY OF THE INVENTION

It is the primary object of the present invention to provide a contra-angle or turbine head of a dental handpiece in which the shank of a dental tool, notably a burr, can be clamped instantaneously and reliably, without play, the setting and removal of the tool being easily accomplished by the practitioner.

For this purpose, the device according to the present invention is characterised in that the claws are provided with ramp means slightly inclined in the direction toward the sleeve axis, that the actuator comprises a slideway provided with other ramp means consistent with and adapted to cooperate with said claw ramp means and axially movable with respect to the sleeve, and a push-button disposed at the upper end of the head and adapted, when depressed, to move said claws to their release position, rolling elements disposed between the ramp means associated with said claws and said slideway for preventing any frictional contact between said claws and said slideway, and coil compression springs disposed concentrically between a member of said slideway and a sleeve stop collar for urging these two members axially away from each other to the clamping position, said two members being moved toward each other when said push-button is depressed.

The principal advantage derived from this device lies in the fact that it is really possible to take up any play, even when relatively broad tolerances are allowed in the manufacture of the tools concerned, this result being obtained by permitting a substantial radial movement of said claws. Since the shanks are plain, the claws must clamp them with a substantial force to permit the transmission of the necessary torque while preserving a resilient force just sufficient to enable the practitioner to handle and change the tools without difficulty. This requirement is met by providing ramp means of extremely moderate slant. Thus, by using relatively weak springs and relatively long stroke, a high radial force can be exerted for clamping the tool shank while permitting a quick and easy release thereof by simply depressing the push-button controlling the coil compression springs.

Other advantages and features characterising the present invention will appear as the following description proceeds with reference to the accompanying drawings illustrating diagrammatically typical forms of embodiment of the invention.

THE DRAWINGS

FIG. 1 is a longitudinal section showing the device in its released condition and incorporated in a contra-angle head;

FIG. 2 is a section taken along the line II—II of FIG. 1, showing the clamping device alone;

FIG. 3 is a section taken along the line III—III of FIG. 2;

FIG. 17 is a longitudinal section showing another modified form of embodiment of the device in its locked condition, and FIG. 18 is a section taken along the line XVIII—XVIII of FIG. 17.

DESCRIPTION OF THE PREFERRED EMBODIMENTS

Reference will now be made to FIGS. 1 to 11 of the drawings showing a first form of embodiment of the improved contra-angle or turbine head of a dental handpiece according to the present invention.

Figure 4:
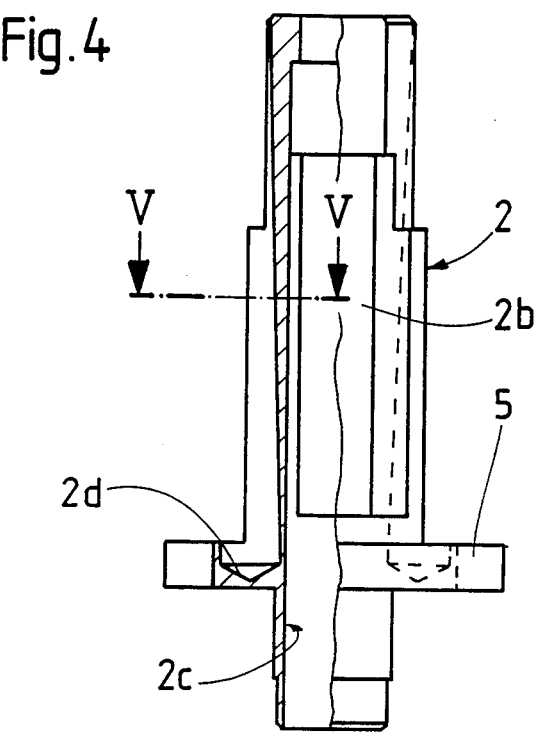
FIG. 4 is a fragmentary longitudinal section showing the sleeve.
Figure 5:
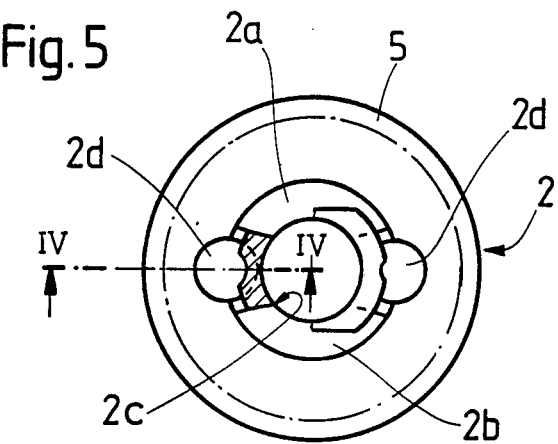
FIG. 5 is a plan view from above of the sleeve, showing a fragmentary section taken along the line V—V of FIG. 4.
Figure 6:
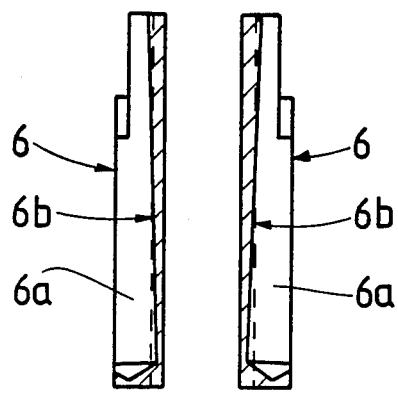
FIG. 6 is a section taken along the line VI—VI of FIG. 7, showing the clamping claws.
Figure 7:
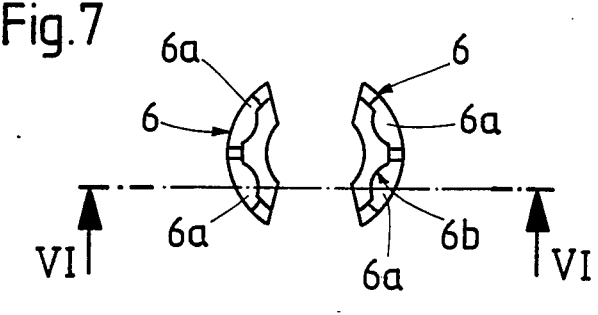
FIG. 7 is a plan view from above of the claws.
Figure 8:
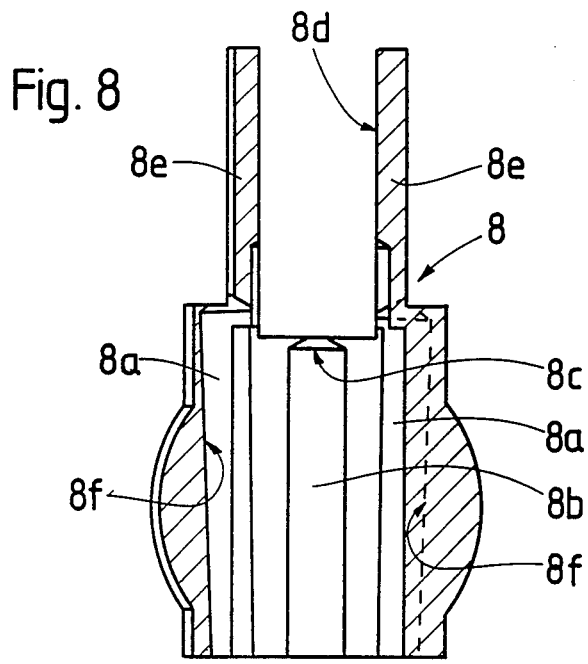
FIG. 8 is a section taken along the broken line VIII—VIII of FIG. 9, showing the clamping socket.
Figure 9:
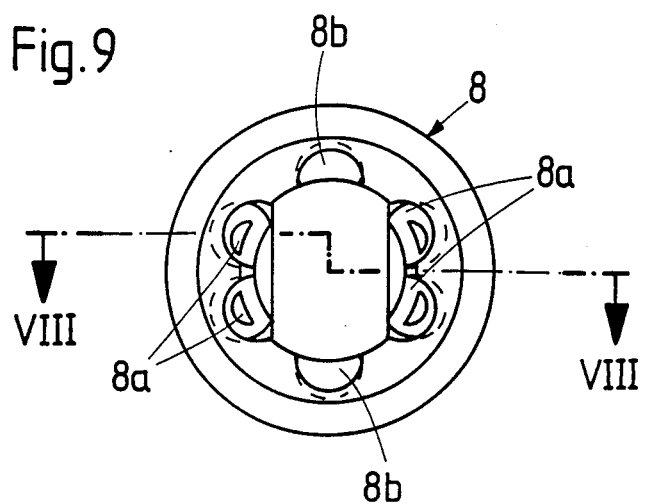
FIG. 9 is a plan view from beneath of the clamping socket.
Figure 10:
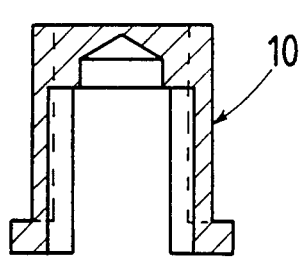
FIG. 10 is a section taken along the line X—X of FIG. 11, showing the upper bearing case.
Figure 11:
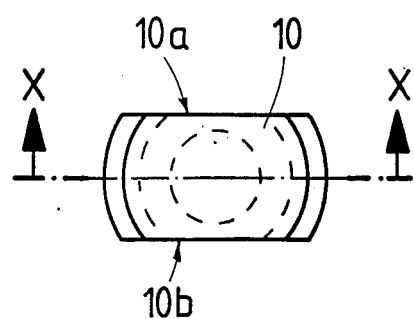
FIG. 11 is a plan view from above of the upper bearing case.

The contra-angle head comprises a case 1 in which a sleeve 2 is rotatably mounted and held by a pair of ball-bearings 3 and 4. This sleeve 2, illustrated in detail in FIGS. 4 and 5, comprises an integral driven pinion 5 somewhat spaced from the lower end of the sleeve. This pinion 5, adapted to mesh with the driving pinion of the drive shaft (not shown), comprises an inner bore 2c corresponding to the diameter of the burr shanks 14 to be fitted therein. It also comprises, intermediate its ends, a pair of diametrally opposed longitudinal recesses 2a,2b adapted to receive corresponding shell-like clamping claws 6 of c-shaped cross section respectively. Each claw 6 (shown separately in FIGS. 6 and 7) comprises a pair of grooves 6a having moderately tapered bottoms converging toward the sleeve axis so as to constitute a pair of opposite ramps 6b. The angle of this ramp 6b to the longitudinal axis of the sleeve is about 2°. A clamping socket 8 illustrated separately in FIGS. 8 and 9 is an easy fit on sleeve 2 and comprises four inner grooves 8a having tapered bottom faces converging likewise toward the longitudinal axis of the socket with an angle of about 2°. These groove bottoms constitute slideways or ramps 8f. The grooves 8a are parallel to the grooves 6a of clamping claws 6 and provide therewith a kind of cage or rampway for rows of balls 9. The grooves 8a are assembled by pairs and between two adjacent pairs another groove having a tapered bottom 8b is provided for receiving a coil compression spring 7 bearing with one and against a shoulder 8c of socket 8 and with the opposite end against the bottom of recesses 2d formed in sleeve 2 between the recesses 2a,2b engaged by the claws 6. In short, two diametrally opposed coil compression springs 7 constantly urge the clamping socket 8 upwards, as seen in the drawings. The upper end of this clamping socket 8 comprises a pair of spaced walls 8e having parallel faces forming a slot 8d in which an upper bearing case 10 shown in detail in FIGS. 10 and 11 is fitted. The function of this upper bearing case 10 is to hold, center and retain the upper end of sleeve 2 in the upper ball-bearing 4. This bearing case 10 has two flat faces 10a, 10b adapted to be fitted between the side walls 8e of socket 8, which form the aforesaid slot 8d.

When assembling the head, firstly the claws 6, sleeve 2, clamping socket 8 and bearing case 10 are assembled, the springs 7 being of course engaged in their recesses before slipping the clamping socket 8 over the sleeve 2. The socket 8 and sleeve 2 are kept in a position such as to be slightly spaced from each other and the balls 9 are introduced into their recesses from the lower face of the socket. The assembly thus obtained is then fitted in bearings 3 and 4, and inserted into the body 1 of the contra-angle or turbine head.

The upper portion of the head body 1 is closed by a ring nut 11 formed with external threads engaging female threads of the body 1 and with a bore slidably engaged by a cap 12 constituting the push-button which, in the normal clamping position illustrated in FIG. 3, is urged away from the upper end of socket 8 by a coil spring 13. In this position, the coil compression springs 7 urge the clamping socket 8 resiliently upwards, so as to push the balls 9 acting in the same direction against the grooves 6a of clamping claws 6. Thus, these claws 6 are moved toward the axis of the assembly and the burr shank 14 introduced into the bore 2c of sleeve 2 is locked in position.

When a slight pressure is exerted on cap 12 as shown in FIG. 1, the spring 13 is compressed and the socket 8 is pushed to a slight extent downwardly, thus compressing the springs 7. The balls 9 are caused to roll in the same direction within the gap, where the distance between the bottom of their recess and the burr shank has its minimum value, due to the slant of ramps 6b of claws 6. Consequently, the claws 6 are expanded to the extent of only a few hundredths of millimeter, thus permitting of releasing the burr shank 14.

Figure 12:
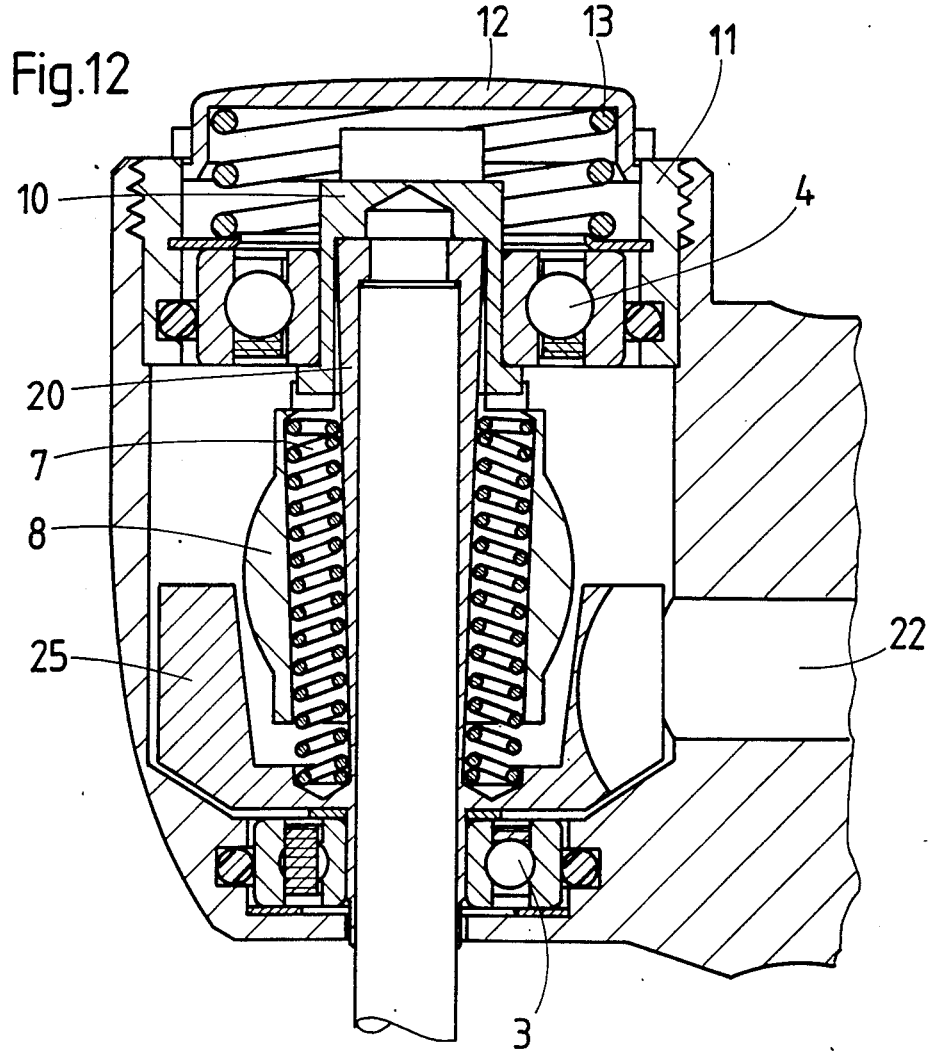
FIG. 12 is a longitudinal section showing the locked device incorporated in a turbine head.

A similar device is applicable of course to a turbine head as illustrated in FIG. 12. The component elements of the device are the same as those described hereinabove and bear the same reference numerals, except for sleeve 20 which, in this case, carries not the teeth of a driven pinion but the blades 25 of a turbine registering with the outlet of a compressed air supply conduit 22.

Figure 13:
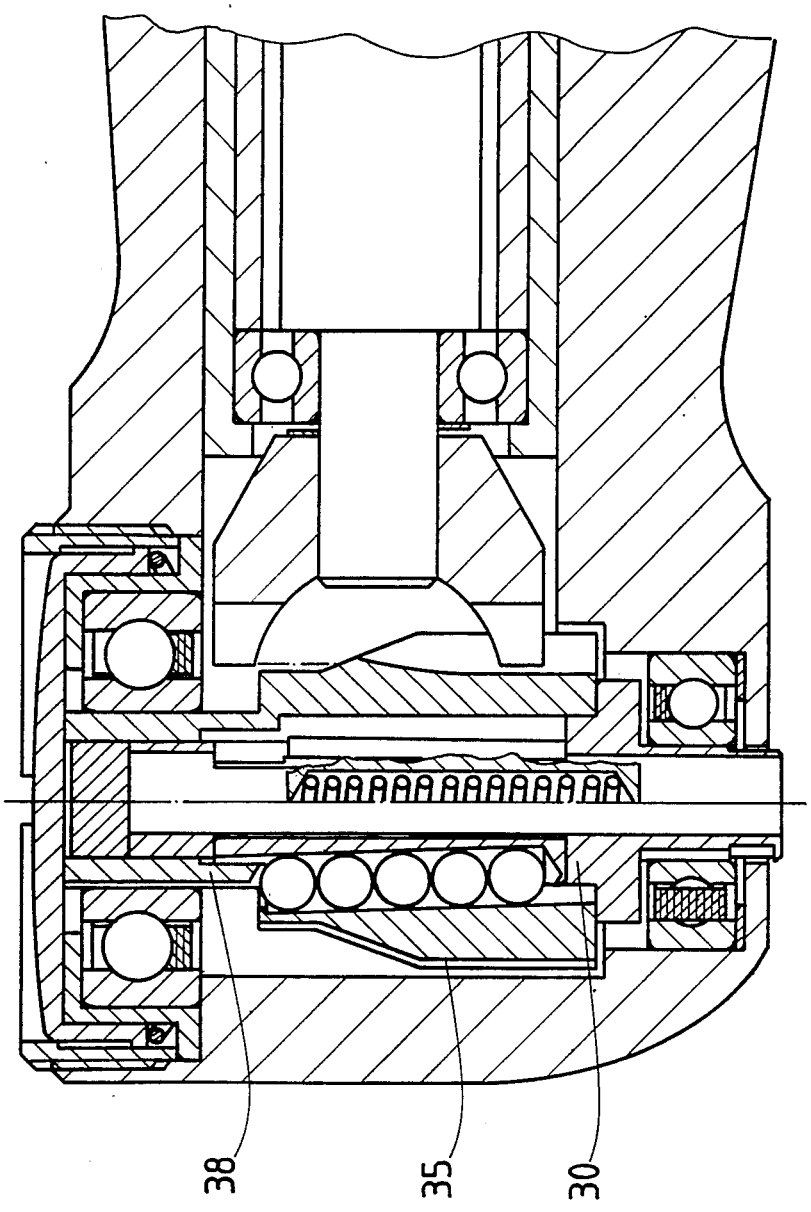
FIG. 13 is a longitudinal section showing a modified form of embodiment of the device in the case of a contra-angle wherein the driving pinion is formed integrally with the outer periphery of the clamping socket.
Figure 14:
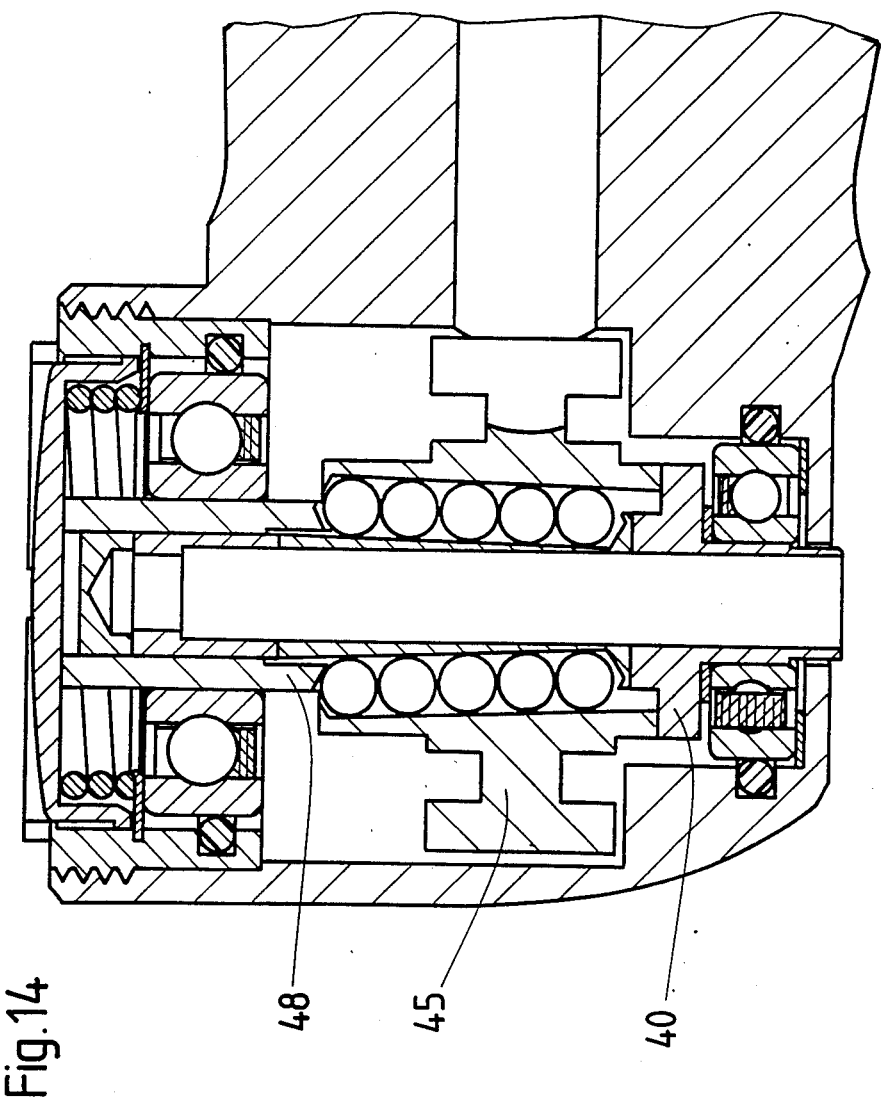
FIG. 14 illustrates the form of embodiment of FIG. 12 in the case of a turbine head, wherein the blades are formed on the outer periphery of the clamping socket.

Various modifications may be brought to the above-described devices. Thus, the driven pinion 35, in the case of a contra-angle (FIG. 13), or the blades 45 in the case of a turbine (FIG. 14), are formed integrally not with the sleeve 30 or 40, respectively, but with the outer periphery of the clamping socket 38 or 48, respectively.

Figure 16:
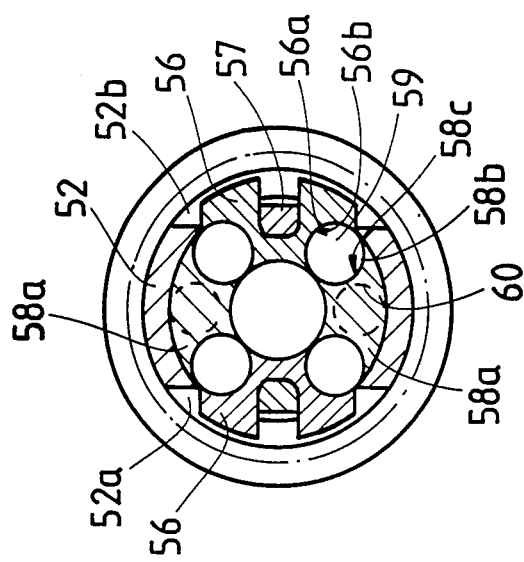
FIG. 16 is a section taken along the line XVI—XVI of FIG. 15.
Figure 15:
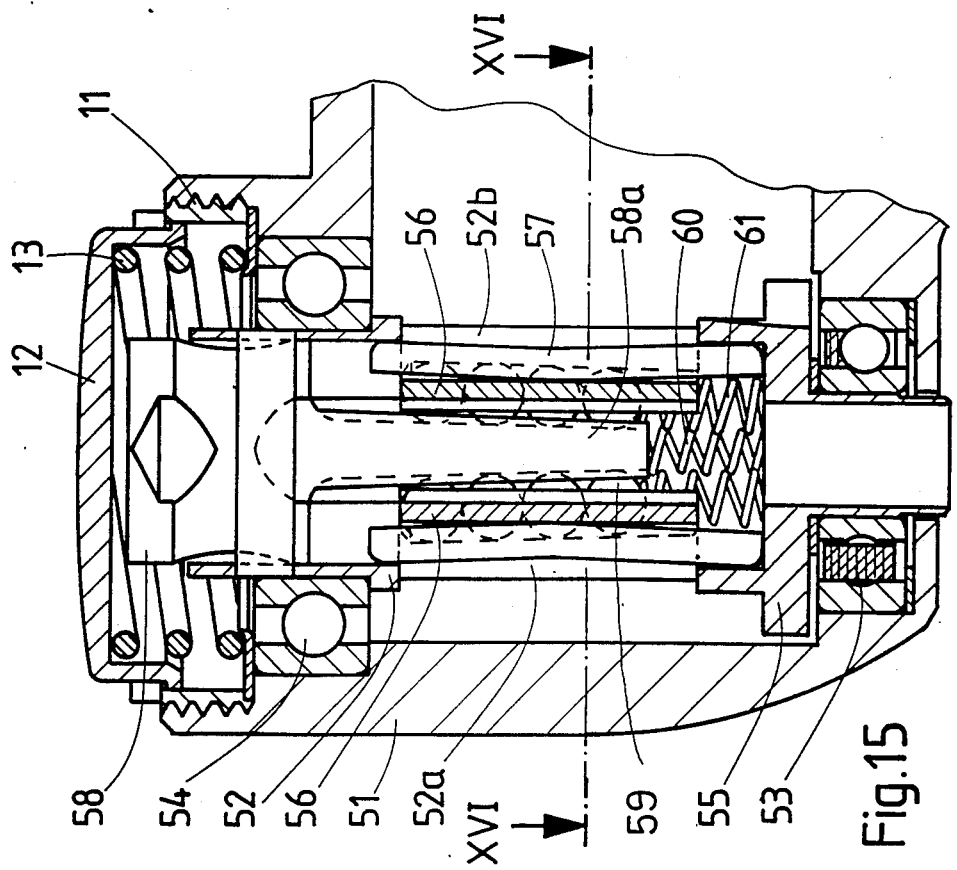
FIG. 15 is a longitudinal section showing another form of embodiment of the device in its locked condition.

Another possible modified form of embodiment of the device is illustrated in FIGS. 15 and 16. In the contra-angle head 51 a sleeve 52 is rotatably mounted in end ball-bearings 53, 54 and provided at its lower end, as in the first example described hereinabove, with a driven pinion 55, and intermediate its ends with a pair of diametrally opposite longitudinal recesses 52a,52b engaged by a pair of shell-like clamping claws 56. Longitudinal grooves 56a having a concave cross-sectional contour are formed in the side walls of said claws 56 to provide a cage for the balls 59. These grooves 56a are inclined so that their bottoms constitute ramps 56b, the general configuration of each claw 56 being substantially that of an inverted V. The claws 56 are normally held in position by spring blades 57.

A release socket 58 which is an easy fit in sleeve 52 comprises a pair of wedge-shaped projections 58a adapted to be inserted between the ramps of clamping claws 56. The inclined side walls of said projections 58a have concave grooves 58b formed therein, and the bottom 58c of these grooves act as slideways to complete the cage means for the balls 59. Each projection 58a is responsive to a spring 60 urging the socket 58 upwardly to its clamping position. The balls 59 are furthermore prevented by springs 61 from vibrating or moving during the rotation of the tool. As in the first form of embodiment described hereinabove the upper portion of the body 51 is closed by a ring nut 11 having slidably mounted therein a cap 12 which, in its normal clamping position, is urged away from the end of socket 58 by a spring 13. In this normal clamping position the socket 58 is urged upwards by springs 60 so as to lift projections 58a and allow the spring blades 57 to press the claws 56 inwards and thus lock the burr shank in position.

During the release operation, the practitioner depresses the cap 12, thus pushing the release socket 58 downwards against the resilient force of springs 60, and its wedge-shaped projections 58a drive the balls 59 downwards, thus moving the clamping claws 56 radially outwards against the resilient force of springs 57. Under these conditions, the burr shank can be released.

FIGS. 17 and 18 illustrate another possible form of embodiment. In this case, the claws 76 consist of the intermediate portion of sleeve 72 proper. For this purpose, the sleeve 72 is provided with two radial notches 73,74 and V-shaped axial slot 75 defining a shell-shaped claw 76 adapted to be engaged by the shank of the dental tool which is held in position by the inherent elasticity of the sleeve material. In the lateral walls of this claw 76 defining said slot 75 longitudinal grooves 76a having a substantially concave configuration are formed to constitute cage means for the balls 75.

A release socket 78 which is an easy fit in sleeve 72 has a wedge-shaped projection 71 adapted to engage the axial slot 75 of the sleeve. The inclined lateral walls of this projection 71 are provided with concave grooves 71a having slideway-forming bottoms for completing the cage means for balls 79. The wedge-shaped projection 71, as in the preceding example, is responsive to a spring 80 constantly urging the socket 78 upwards to its clamping position. Other springs 81 prevent the balls 79 from vibrating during the rotation of the dental tool. The assembly comprising the sleeve 72 and socket 78 is rotatably mounted in the head case 70 by means of ball-bearings 82,83.

In the normal clamping position illustrated in FIG. 17 the socket 78 is urged upwards by spring 80, so that the wedge-shaped projection 71 of slot 75 is released and the clamping claw 76 is allowed to actuate the shank of the dental tool while retaining this shank by virtue of its inherent resiliency. During the release step, the socket 78 can be moved downwards by a push-button device 12,13 similar to the push-button means of the above-described forms of embodiment, so that the projection 71 is caused to engage the slot 75 and the balls 79 are driven downwards while expanding the claws 76 radially outwards against the resistance of its inherent resiliency.

Of course, other forms of embodiment may be contemplated without departing from the basic features and principles of the invention as claimed in the appended claims.

What is claimed is:

1. A head of a dental hand piece comprising a head case, a chuck for receiving a smooth shank of a dental tool rotatably mounted in said case, means for driving said chuck in rotation about an axis, said chuck comprising a sleeve adapted to receive a smooth shank of a dental tool and provided with at least one elongate, axially extending clamping claw movable radially between an inner position for clamping said dental tool shank and an outer position for releasing said dental tool shank, an actuating member movable axially relative to said sleeve, said actuating member and clamping claw having in opposed surfaces elongate longitudinal grooves which face one another to form an elongate ramp way for rolling elements, an plurality of rolling elements disposed in a row in said ramp way, said ramp way extending in a generally axial direction but inclined at a small angle to said axis of rotation in such manner that axial movement of said actuating member relative to said sleeve acts through said ramp way and rolling elements to produce radial movement of said clamping claw, means for resiliently urging said clamping claw inwardly toward said clamping position and releasing means for manually moving said actuating member axially relative to said sleeve in a direction to move said clamping claw radially outwardly to said outer releasing position.

2. A head for a dental handpiece according to claim 1, in which the angle of inclination of said ramp way relative to the axis of rotation of said chuck is between 1° and 4°.

3. A head for a dental handpiece according to claim 2, in which the angle of inclination of said ramp way relative to said axis is approximately 2°.

4. A head for a dental handpiece according to claim 1, in which said releasing means comprises a cup-shaped button mounted in said case above said chuck for movement axially of said chuck and spring means for resiliently holding said button in an upper position, said button being manually movable downward against the action of said spring means to move said actuating member to releasing position.

5. A head for a dental handpiece according to claim 1, in which said means for driving said chuck in rotation comprises pinion teeth on said sleeve.

6. A head for a dental handpiece according to claim 1, in which said means for driving said chuck in rotation comprises pinion teeth on said actuating member.

7. A head for a dental handpiece according to claim 1, in which said means for driving said chuck in rotation comprises turbine blades on said sleeve.

8. A head for a dental handpiece according to claim 1, in which said means for driving said chuck in rotation comprises turbine blades on said actuating member.

9. A head for dental handpiece according to claim 1, in which said sleeve has therein a plurality of circumferentially spaced axially extending recesses in which a like plurality of said clamping claws are respectively disposed, and in which said actuating member comprises a clamping socket surrounding said sleeve and clamping claws, a plurality of said ramp ways for said rolling elements comprising facing grooves in radially outer surfaces of said clamping socket and inclined upwardly and inwardly toward said axis in such manner that upward movement of said clamping socket forces said clamping claws inwardly, and said means for resiliently urging said clamping claws radially inwardly comprising coil compression springs disposed in axially extending recesses in said clamping socket and acting to urge said clamping socket upwardly.

10. A head for a dental handpiece according to claim 9, in which said clamping claws are C-shaped in cross section and have a pair of said grooves in their outer surfaces, said clamping socket having in its inner surface matching grooves to form said ramp ways for said rolling elements.

11. A head for a dental handpiece according to claim 9, in which said clamping socket has at its upper end two diametrically opposite upward projections separated by diametrically opposite slots and in which an upper bearing case for said sleeve has two flat faces received in said slots.

12. A head for a dental handpiece according to claim 1, in which said sleeve has, intermediate its ends, a pair of diametrically opposite longitudinal recesses in which a pair of said clamping claws are respectively disposed, and in which said means for resiliently urging said clamping claws inwardly comprise spring blades received in longitudinal grooves in radially outer surfaces of said clamping claws and having ends anchored to end portions of said sleeve, said actuating member comprising a release socket having a pair of wedge-shaped projections extending down in said sleeve between said clamping claws, longitudinal grooves in said projections and matching longitudinal grooves in said clamping claws forming ramp ways for said rolling elements, said ramp ways being slightly inclined to said axis in such manner that downward movement of said release socket forces said clamping claws radially outwardly against resilient force exerted by said spring blades.

13. A head for a dental handpiece according to claim 12, further comprising coil compression springs disposed in longitudinal recesses in said projections of said release socket and acting between said release socket and said sleeve to urge said release socket upwardly to clamping position.

14. A head for a dental headpiece according to claim 13, further comprising compression coil springs disposed in said ramp ways and acting between said sleeve and said rolling elements to prevent vibration of said rolling elements.

15. A head for a dental handpiece according to claim 1, in which said sleeve has two radial slots spaced inwardly from opposite ends of the sleeve and a longitudinal V-shaped slot extending between said radial slots to define a resilient clamping claw integral with said sleeve, and in which said actuating member comprises a release socket having a wedge-shaped projection extending down in said longitudinal slot of said sleeve with facing grooves in said edges of said projection and side edges of said longitudinal slot defining ramp ways for said rolling elements, said ramp ways being slightly inclined to said axis in such manner that downward movement of said release socket forces said clamping claw radially outwardly against inherent resiliency of said clamping claw and sleeve.

16. A head for a dental handpiece according to claim 15, further comprising a compression coil spring disposed in a longitudinal recess in said projection and acting between said sleeve and said rolling elements to prevent said rolling elements from vibrating.

* * * * *